(12) United States Patent
Wilson et al.

(10) Patent No.: US 10,499,865 B2
(45) Date of Patent: Dec. 10, 2019

(54) METHODS FOR PHYSIOLOGICAL STATE DETERMINATION IN BODY SCANS

(71) Applicant: HOLOGIC, INC., Bedford, MA (US)

(72) Inventors: Kevin Wilson, Bedford, MA (US); Thomas Kelly, Bedford, MA (US)

(73) Assignee: Hologic, Inc., Marlborough, MA (US)

( * ) Notice: Subject to any disclaimer, the term of this patent is extended or adjusted under 35 U.S.C. 154(b) by 81 days.

(21) Appl. No.: 15/553,748

(22) PCT Filed: Feb. 25, 2016

(86) PCT No.: PCT/US2016/019562
§ 371 (c)(1),
(2) Date: Aug. 25, 2017

(87) PCT Pub. No.: WO2016/138262
PCT Pub. Date: Sep. 1, 2016

(65) Prior Publication Data
US 2018/0049710 A1 Feb. 22, 2018

Related U.S. Application Data

(60) Provisional application No. 61/121,197, filed on Feb. 26, 2015.

(51) Int. Cl.
*A61B 6/00* (2006.01)
*G06T 7/00* (2017.01)

(52) U.S. Cl.
CPC .............. *A61B 6/482* (2013.01); *A61B 6/405* (2013.01); *A61B 6/50* (2013.01); *A61B 6/5217* (2013.01); *A61B 6/4035* (2013.01); *G06T 7/0012* (2013.01)

(58) Field of Classification Search
CPC ....... A61B 6/482; A61B 6/5217; A61B 6/405; A61B 6/50; A61B 6/4035; G06T 7/0012
See application file for complete search history.

(56) References Cited

U.S. PATENT DOCUMENTS

| | | | |
|---|---|---|---|
| 4,831,527 A * | 5/1989 | Clark | A61B 5/1075 600/553 |
| 6,081,582 A | 6/2000 | Mazess et al. | |

(Continued)

OTHER PUBLICATIONS

International Search Report and Written Opinion of the International Searching Authority for corresponding International Patent Application No. PCT/US2016/019562 dated Jul. 21, 2016, 15 pages.

(Continued)

*Primary Examiner* — Qian Yang

(57) ABSTRACT

A system for measuring muscle mass of a patient has a dual-energy radiation emission source. A radiation detector is configured to detect radiation emitted from the dual-energy radiation emission source passed through the patient. A processor has a memory with storing instructions, that when executed by the processor, perform a set of operations. The operations include receiving radiation detection data; generating a scan representation; identifying a primary fat target; determining an amount of fat in the primary fat target; comparing the amount of fat in the primary fat target to a reference; and based on the comparison, correcting an estimated amount of lean tissue to generate a corrected muscle mass value.

20 Claims, 11 Drawing Sheets

(56) References Cited

U.S. PATENT DOCUMENTS

| | | | |
|---|---|---|---|
| 6,173,034 B1* | 1/2001 | Chao | A61B 6/482 378/37 |
| 7,725,153 B2 | 5/2010 | Kelly et al. | |
| 8,300,911 B1* | 10/2012 | Payne | A61B 6/482 128/922 |
| 8,792,689 B2 | 7/2014 | Kelly et al. | |
| 9,179,873 B2 | 11/2015 | Kelly et al. | |
| 9,642,585 B2 | 5/2017 | Wilson | |
| 2006/0074288 A1 | 4/2006 | Kelly et al. | |
| 2010/0234719 A1 | 9/2010 | Kelly et al. | |
| 2011/0235886 A1 | 9/2011 | Kelly et al. | |
| 2014/0371570 A1* | 12/2014 | Davis | A61B 5/4244 600/407 |
| 2017/0046837 A1* | 2/2017 | Leinhard | A61B 5/055 |

OTHER PUBLICATIONS

Lehmann, L.A. et al., "Generalized image combinations in dual KVP digital radiography", Med. Phys. 8(5): 659-667 (1981).

Lustgarten, M.S. et al., "Assessment of Analytical Methods Used to Measure Changes in Body Composition in the Elderly and Recommendations for Their Use in Phase II Clinical Trials", J. Nutr. Health Aging, 15(5): 368-375 (2011).

Pietrobelli, A. et al., "Dual-energy X-ray absorptiometry: fat estimation errors due to variation in soft tissue hydration", The American Physiological Society, E808-E816 (1998).

Prado, C. et al., "Lean Tissue Imaging: A New Era for Nutritional Assessment and Intervention", Journal of Parental and Enteral Nutrition, 38(8): 940-953 (2014).

Sayer, A.A. et al., "New horizons in the pathogenesis, diagnosis and management of sarcopenia", Age and Ageing, 42: 145-150 (2013).

Sorenson, J.A. et al., "Simulation of dual-energy x-ray absorptiometry", Medical Physics, 16(1): 75-80 (1989).

Wear, J. et al., "CZT detector for dual-energy x-ray absorptiometry (DEXA)", Proceedings of SPIE, 4142: 175-188 (2000).

PCT International Preliminary Report on Patentabiiity in International Application PCT/US2016/019562, dated Aug. 29, 2017, 8 pgs.

* cited by examiner

METHODS FOR PHYSIOLOGICAL STATE DETERMINATION IN BODY SCANS

This application is a National Stage Application of PCT/US2016/019562, filed Feb. 25, 2016, which claims priority to U.S. Provisional Patent Application 62/121,197, filed Feb. 26, 2015, the disclosures of which are hereby incorporated by reference herein in their entireties. To the extent appropriate, a claim of priority is made to each of the above disclosed applications.

This application is related to U.S. patent application Ser. No. 14/553,533, filed Nov. 25, 2014, entitled "Bone Densitometer," the disclosure of which is hereby incorporated by reference herein in its entirety.

BACKGROUND

Scanning radiographic equipment differs from conventional radiography in that it employs a narrowly collimated beam of radiation, typically x-rays, formed into, for example, a pencil beam, a narrow fan beam, or a broad fan beam, rather than a broad area cone beam. The compact beam size allows the replacement of an image forming sheet of radiographic film, used with conventional radiographic equipment, with a small area array of electronic detector elements. Further, the scanning allows the collection of data over a much broader area than would be practical with a single x-ray cone beam. The electronic detector elements receiving the transmitted radiation produce electrical signals which may be discriminated by pulse height into various pulse height bins and counted or charge collected and converted to digital values by an analog-to-digital converter for the later development of an image or for other processing by computer equipment.

SUMMARY

The ability to quantify the measurement of the transmitted radiation, implicit in the digitization, allows not only the formation of a radiographic "attenuation" image but also the mathematical analysis of the composition of the attenuating material by dual energy techniques. Such dual energy techniques quantitatively compare the attenuation of radiation at two energies to distinguish, for example, between bone and soft tissue, or fatty tissue and lean tissue. The information derived from scans of the body or portions thereof can be utilized to determine various physiological conditions, such as edema, and to use those physiological conditions to correct measurements or determinations of lean tissue, such as muscle. This determination can be used to accurately diagnose pathological states of the body.

In one aspect, the technology relates to a system for measuring muscle mass of a patient, the system having: a dual-energy radiation emission source; a radiation detector configured so as to detect radiation emitted from the dual-energy radiation emission source passed through the patient; at least one processor; and a memory coupled to the at least one processor, the memory storing instructions that when executed by the at least one processor, perform a set of operations including: receiving radiation detection data from the radiation detector; based on the radiation detection data, generating a scan representation; identifying a primary fat target in the scan representation; determining an amount of fat in the primary fat target; comparing the amount of fat in the primary fat target to a reference; and based on the comparison, correcting an estimated amount of lean tissue to generate a corrected muscle mass value. In an embodiment, the primary fat target is in a region of interest and the corrected muscle mass value is for the region of interest. In another embodiment, the primary fat target is for a first region of the patient and the corrected muscle mass value is for a second region of the patient. In yet another embodiment, the first region is a torso region of the patient and the second region is an appendage of the patient.

In another aspect, the technology relates to a system for measuring muscle mass of a patient, the system having: a dual-energy radiation emission source; a radiation detector configured so as to detect radiation emitted from the dual-energy radiation emission source passed through the patient; at least one processor; and a memory coupled to the at least one processor, the memory storing instructions that when executed by the at least one processor, perform a set of operations including: receiving radiation detection data from the radiation detector; based on the radiation detection data, generating a scan representation; estimating an amount of lean tissue in a region of interest; identifying a primary fat target in the scan representation in the region of interest; determining an amount of fat tissue in the primary fat target; determining an amount of lean tissue in the primary fat target; and correcting the estimated amount of lean tissue in the region of interest based on the amount of lean tissue in the primary fat target to generate a corrected muscle mass value.

In another aspect, the technology relates to a system for measuring muscle mass of a patient, the system having: a dual-energy radiation emission source; a radiation detector configured so as to detect radiation emitted from the dual-energy radiation emission source passed through the patient; at least one processor; and a memory coupled to the at least one processor, the memory storing instructions that when executed by the at least one processor, perform a set of operations including: receiving radiation detection data from the radiation detector; based on the radiation detection data, generating a scan representation; estimating an amount of lean tissue in a region of interest; identifying a primary fat target in the region of interest in the scan representation; determining an amount of fat tissue in the primary fat target; determining an amount of lean tissue in the primary fat target; using the lean mass and fat mass in the primary fat target to determine a correction for the hydration of the fat mass (Ef) and a correction of the hydration of the lean mass (El); and correcting the estimated amount of lean tissue based on subtracting the product of Ef and the determined amount of fat tissue from the product of Ef and the estimated amount of lean tissue in the region of interest. In an embodiment, the set of operations further includes comparing the amount of fat tissue in the primary fat target to a reference amount. In another embodiment, the set of operations further includes, based on the comparison, correcting the estimated amount of lean tissue in the region of interest to generate a corrected muscle mass value. In yet another embodiment, the region of interest is an appendage. In still another embodiment, the primary fat target is a subcutaneous fat region. In another embodiment, the set of operations further includes: modeling the subcutaneous fat layer; and removing the subcutaneous fat layer from the estimated amount of lean tissue.

In another aspect, the technology relates to a method for determining muscle mass of a patient, the method including: detecting, by a radiation detector, a radiation emission from a densitometer passed through the patient; based on the detected radiation emission, generating a scan representation of a region of interest of the patient, the scan representation including one or more pixels; determining, by a processor, an estimated amount of lean tissue in the region of interest; identifying, by the processor, a primary fat target within the region of interest; identifying, by the processor, a pixel in the scan representation representative of the primary fat target; analyzing, by the processor, the pixel representative of the primary fat target to determine an amount of fat in the primary fat target; comparing, by the processor, the determined amount of fat to a reference amount; correcting, by the processor, the estimated amount of lean tissue based at least in part on the comparison to generate a corrected muscle mass value for the region of interest of the patient; and displaying the corrected muscle mass value for the region of interest. In an embodiment, the method further includes analyzing the pixel representative of the primary fat target to determine an amount of water present in the primary fat target. In another embodiment, the method further includes: determining model of the primary fat target based on at least a depth of the primary fat target; and subtracting the modeled primary fat target from the estimated amount of lean tissue.

In another aspect, the technology relates to a method for identifying a condition in a patient, the method including: detecting, by a detector, a beam of radiation having passed through the patient; based on the detected beam of radiation, generating a scan representation including one or more pixels; identifying, by a processor, a primary fat target in the scan representation; analyzing, by the processor, at least one pixel within the scan representation to determine an amount of at least one of fat and water in the primary fat target; comparing, by the processor, the determined amount to a reference amount; based on the comparison, generating, by the processor, a condition indicator; and displaying the condition indicator on a user interface. In an embodiment, the condition indicator corresponds to a localized edema in a region of interest of the patient. In another embodiment, the condition indicator is displayed on a user interface operatively coupled to a densitometer. In yet another embodiment, the region of interest is an appendage. In still another embodiment, the reference amount is determined from a set of sample persons. In another embodiment, the primary fat target is a subcutaneous fat region.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Non-limiting examples of various systems and methods utilized for imaging of bodies or parts thereof, and using the information gathered from said systems and methods for analysis, include:

U.S. patent application Ser. No. 14/553,533, filed Nov. 25, 2014, entitled "Bone Densitometer"

U.S. Pat. Nos. 6,081,582; 7,725,153; 8,792,689; and 9,179,873

U.S. Published Patent Application Nos. 2011/0235886 and 2010/0234719

WEAR, James et al., "CZT detector for dual energy x-ray absorptiometry (DEXA)", Proceedings of SPIE Vol. 4142, Penetrating Radiation Systems and Applications II, (Dec. 18, 2000), pages 175-188

LEHMANN, L. A. et al., "Generalized image combinations in dual KVP digital radiology", Medical Physics, Vol. 8, No. 5, September/October 1981, pages 659-667

SORENSON, James A. et al., "Simulation studies of dual-energy x-ray absorptiometry", Medical Physics, Vol. 16. No. 1, January/February 1989, pages 75-80

The disclosures of each of the above-identified patents and publications are hereby incorporated by reference herein in their entireties.

Pathologies and physiological conditions described in the present application are further described in the following:

LUSTGARTEN, M. S. et al., "Assessment of analytical methods used to measure changes in body composition in the elderly and recommendations for their use in Phase II clinical trials", J. Nutr. Health Aging, May 2011, 15(5): 368-375

SAYER, Avan Aihie et al., "New horizons in the pathogenesis, diagnosis and management of sarcopenia", Age and Ageing Jan. 11, 2013, 42: pages 145-150

The disclosures of each of the above-identified patents and publications are hereby incorporated by reference herein in their entireties.

The present technology provides a system and methods suitable for transverse scanning of at least a portion of a patient so as to determine the amounts of various tissue (fatty, lean) and bone in the patient. With this information, accurate determinations of physiological conditions of the patient can be made. The technologies described herein may be leveraged with other types of imaging procedures. Indeed, any imaging procedures that merge multiple images into a single image may benefit from the described technologies. Although the imaging systems described below refer generally to imaging and determining the body composition of soft tissue e.g. fat and lean, other types of tissues can be detected and this information leveraged as described herein.

Figure 1:
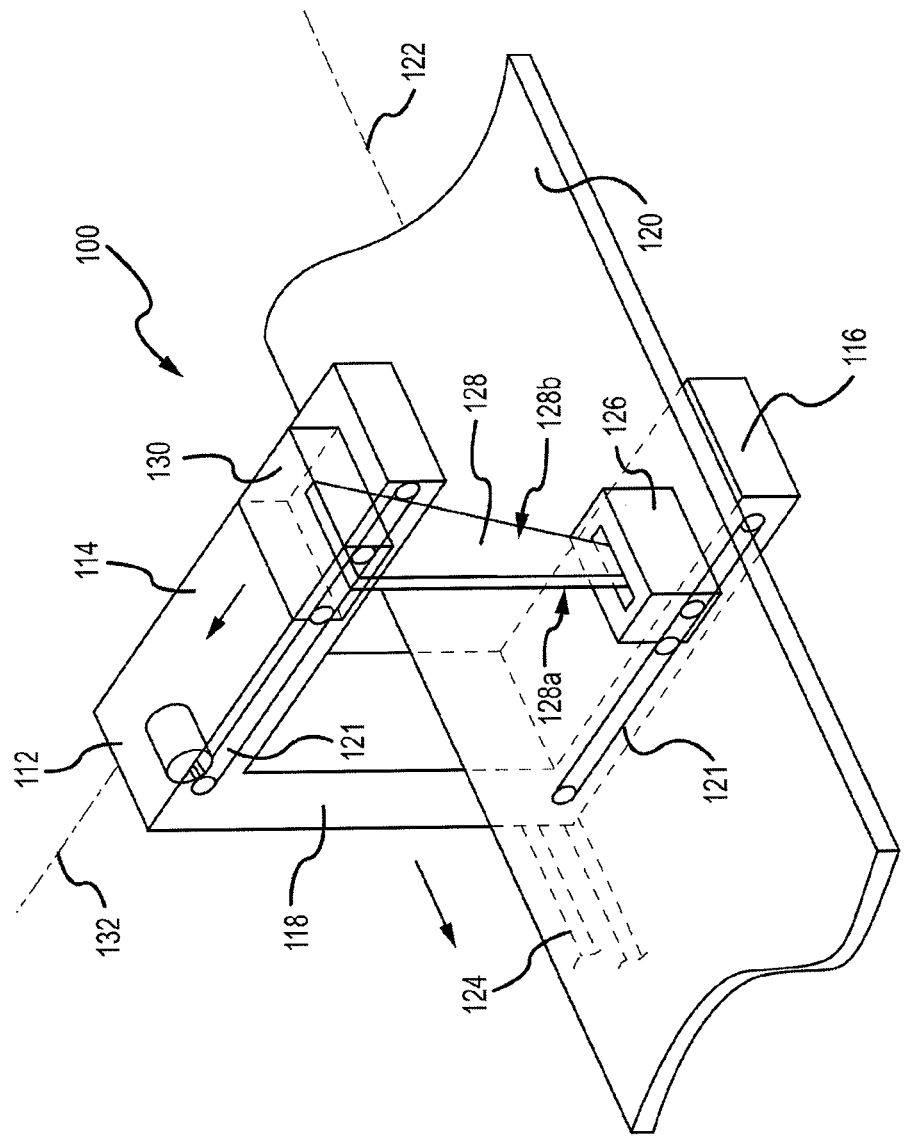
FIG. 1 depicts a perspective view of a transverse scanning densitometer in accordance with one embodiment of the technology.

FIG. 1 depicts a perspective view of a transverse scanning densitometer 100 in accordance with one embodiment of the technology. The densitometer 100 may also be referred to herein as a dual-energy x-ray absorptiometry (DXA)

machine. The densitometer 110 includes a support arm 112 having vertically opposed horizontal arms 114 and 116 separated by vertical bar 118. A horizontal planar patient support table 120 is disposed between the horizontal arms 114, 116 and extends along a longitudinal axis 122. A belt drive system 124 of a type well known in the art, allows motion of the support arm 112 longitudinally along longitudinal axis 122 for the length of the table 120. In other embodiments, other types of drive systems, including racks and gears, may be utilized. The longitudinal axis 122 of the table 120 is generally substantially parallel to a longitudinal axis of a patient lying on the table 120.

An x-ray source 126 is within the lower arm 116. The x-ray source emits a collimated fan beam 128 of x-rays directed upward through the table 120. The beam 128 is detected or otherwise received by a linear detector 130. The fan beam 128 is oriented so that its narrowest extent 128a is along a transverse axis 132 and its widest extent is along the longitudinal axis 122. The table 120 is generally radiolucent so as to provide a support surface without significantly affecting the attenuation of the fan beam 128.

The x-ray source 126 and linear detector 130 may be moved transversely along the transverse axis 132. The x-ray source 126 and linear detector 130 are configured so as to move along the arms 114 and 116. This movement allows for transverse scans of the patient on the table 120. Motion of the x-ray source 126 and detector 130 is synchronized by belt-drive actuation mechanisms 121 as will be well understood to those of ordinary skill in the art. As with the belt drive system 124 described above, other types of drive mechanisms can be utilized in place of the belt-drive actuation mechanisms 124.

Figure 2:
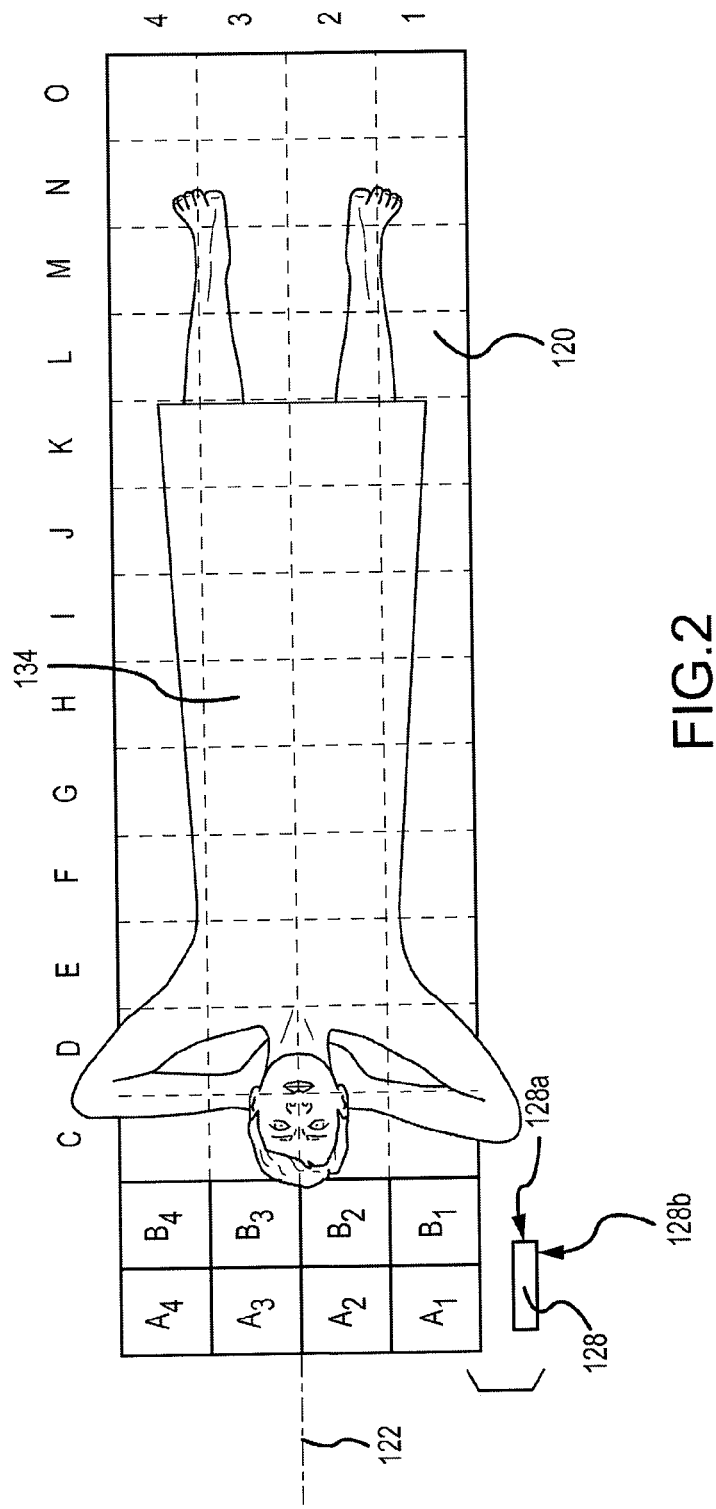
FIG. 2 depicts a top plan view of the table of the transverse scanning densitometer of FIG. 1.

FIG. 2 depicts a top plan view of the table 120 of the transverse scanning densitometer of FIG. 1. Certain of the components described above are not depicted in FIG. 2 for clarity. The fan beam 128 may be scanned over the surface of table 120 and hence may scan the whole body of patient 134 so as to generate a series of transversely extending scan images that may be merged into a single composite image or data set. Alternatively, a plurality of scan images can be merged into a single composite image for a particular body structure or part. For example, a first scan image may encompass, in sequence, areas A1, A2, A3, and A4. The x-ray source and linear detector, described above, may move transversely as required, emitting and receiving x-ray energy along the various sequential areas. At the end of this scan, motion of the support arm, described above, in the longitudinal direction may be performed. For example, the support arm may move towards the feet of the patient, so as to align with a second area of the patient such that the detector may perform a second scan image. The second scan image may be in order of areas B4, B3, B2, and B1. Alternatively, the arm may return to the side of the table 120 where it began the first image scan and scan areas B1, B2, B3, and B4. Because the transverse width of the patient 134 is substantially less than the superior to inferior height of the patient, each scan image, e.g., all of areas 1-4 in each of path A or path B, is acquired at a time closely proximate to its adjacent scan images and thus the risk of patient motion and the amount of patient motion may be substantially reduced. This is one of several marked advantages over imaging systems that that perform scans along the longitudinal axis of the patient.

In other embodiments, transverse scans of particular body parts may be performed. In one example, a complete transverse scan of the ribcage may include scans along scan paths E, F, G, and H. A transverse scan of a single body part that does not extend across an entire transverse scan path can also be performed. For example, the left femur may be scanned by imaging areas I1, I2, J2, J1, K1, and K2. Other transverse scan paths are contemplated.

The radiation source 126 may be a radioisotope or an x-ray tube running at constant voltage to produce a polyenergetic radiation beam. The beam may be subsequently filtered with a K-edge filter to form two energy modes. Alternatively, the radiation source 126 may be an x-ray tube run in a switched voltage mode where the voltage on the x-ray tube is periodically changed from a high to low voltage shifting the energy spectrum of the produced x-ray beam. Data is acquired by a broad band detector 130 and is sequentially high and low energy data as may be used in dual energy measurements. Other techniques including rotating filter wheels and the like may be used to produce sequential dual energy beams. The detector 130 may also include detection elements for detecting high energy radiation and detection elements for detecting low energy radiation. A user interface include a display and other input/output options, such as those discussed below with reference to FIGS. 8-9, may be operatively coupled to the densitometer 100 for displaying results or other information gathered or generated by the densitometer, as discussed herein. For instance, the user interface may be operatively coupled through a network or wired connection to the densitometer 100.

Figure 3:
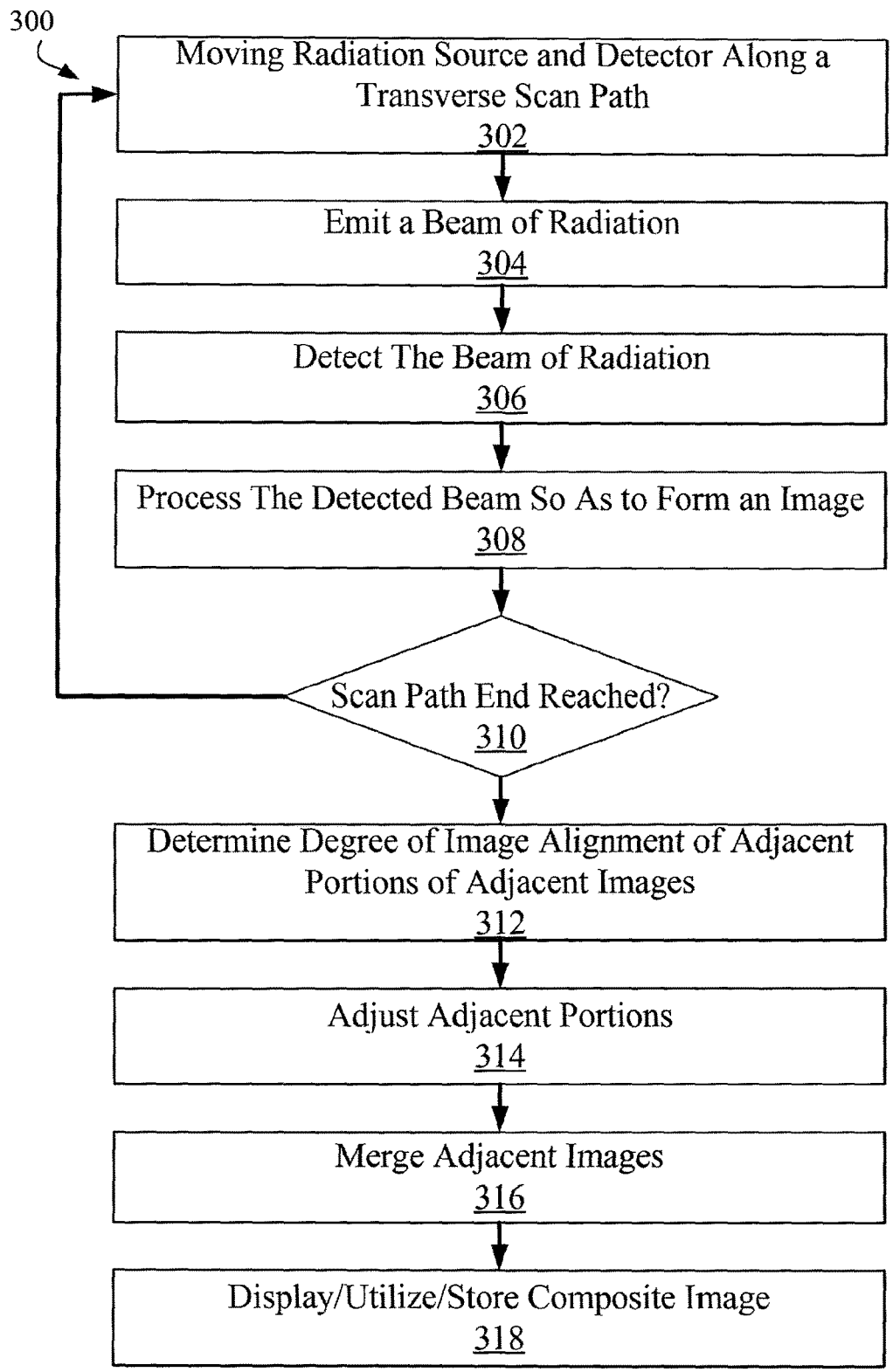
FIG. 3 depicts a method of generating images during a transverse scanning procedure in accordance with an embodiment of the technology.

FIG. 3 depicts a method 300 of generating images during a transverse scanning procedure in accordance with an embodiment of the technology. The method 300 provides for a scanning densitometer having a radiation source collimated to produce or emit a beam of radiation directed across a patient to an electronic radiation detector, the latter of which receives, detects, or otherwise measures the beam of radiation passing through the patient. A scanning assembly moves the radiation source and radiation detector along at least one scan path transverse to a longitudinal axis of a patient, operation 302. While moving, the radiation source emits the beam of radiation, operation 304, which is detected by the radiation detector, operation 306. The detected beam is then processed so as to form an image, operation 308. Since the beam has a predefined width, the size of each image is based on the beam width and a length of travel of the scanning assembly. Any number of discrete images may be formed as the scanning assembly travels along the transverse scan path. As the scanning assembly traverses the scan path, one or more sensors determine a position thereof. If the end of the scan path is not reached as depicted in operation 310, flow branches to NO and movement of the scanning assembly (as well as operations 302-308) continue, thus generating a plurality of images along the scan path. Once the end of the scan path is reached at operation 410, flow branches YES, where a degree of image alignment is then determined at operation 312.

In certain embodiments, the image alignment of adjacent portions of adjacent images is determined. The size of the adjacent portions may be determined based on, e.g., number of pixels in the image, a percentage of the total area of the image, or other factors. These adjacent portions of the adjacent images may be adjusted, operation 314, so as to allow different degrees of overlap to better match structures within the images having various heights within the patient. The degree of image alignment may evaluate only the bone portion of the image, only a lean tissue portion of the image, only a fat tissue portion of the image, or a combination of any of the three. The method 400 may improve the ability to match the images by eliminating structure such as soft tissue whose matching is not critical. In other embodiments, determining the degree of image alignment may include determining a structure height based on a known divergence of the radiation beams and the determined overlap, thus improving image alignment. The height may be used to scale each scan image prior to merging adjacent scan images. Thus, the system and method described herein may employ the difference in overlap between adjacent scan images to correct the magnification of the image. Thereafter, the adjacent images are merged at overlapping areas, operation 316, to form a composite image that includes all of the combined adjacent images. Prior to merging, the images may be weighted so as to eliminate any disproportionate influence of redundant data in the images. Regardless, the proposed technologies do not rely on weighting alone, as such methods may produce a blurring of the merged image. Blurring of the image may be reduced or eliminated by correcting overlap of the images, as described herein. This composite image has an overlap corresponding to a best matching of the plurality of scan images. In operation 318, the composite image may then be stored, displayed, and/or otherwise utilized for marking and analysis of tissue, as described herein.

The patient support may support a supine patient with the patient's head and feet lying along a longitudinal axis and the scanning assembly may move the radiation source and electronic detector along a series of transverse scan paths substantially perpendicular to the longitudinal axis across the patient to acquire the scan images. Such a method includes operations similar those depicted in FIG. 3. As the end of a scan path is reached, the system may then traverse a second transverse scan path that is substantially parallel to the first transverse scan path. Images obtained along the second transverse scanned path are processed as described in FIG. 3, operations 312-316. However, degree of image alignment may be determined for both of adjacent images in the same scan path, as well as adjacent images in adjacent scan paths. Such processing can produce a master composite image that includes all images in all scan paths, which may then be utilized as described herein.

Images obtained from various imaging systems, such as those referred to herein, can divide the body into three components: fat tissue, lean ("lipid-free soft tissue") tissue, and bone mineral content ("BMC"). Systems that emit dual energies during an imaging or scanning sequence may generally be utilized to identify a maximum of two of those components at a time. For example, in areas of the body where bone is primarily located, BMC may be identified as described generally herein. In areas without bone, fat tissue and lean may be identified. Similarly, in primary fat regions that are substantially without lean tissue, such as subcutaneous fat regions, fat tissue and non-fat material can be identified. In those primary fat regions, the non-fat material is principally composed of water.

Figure 4:
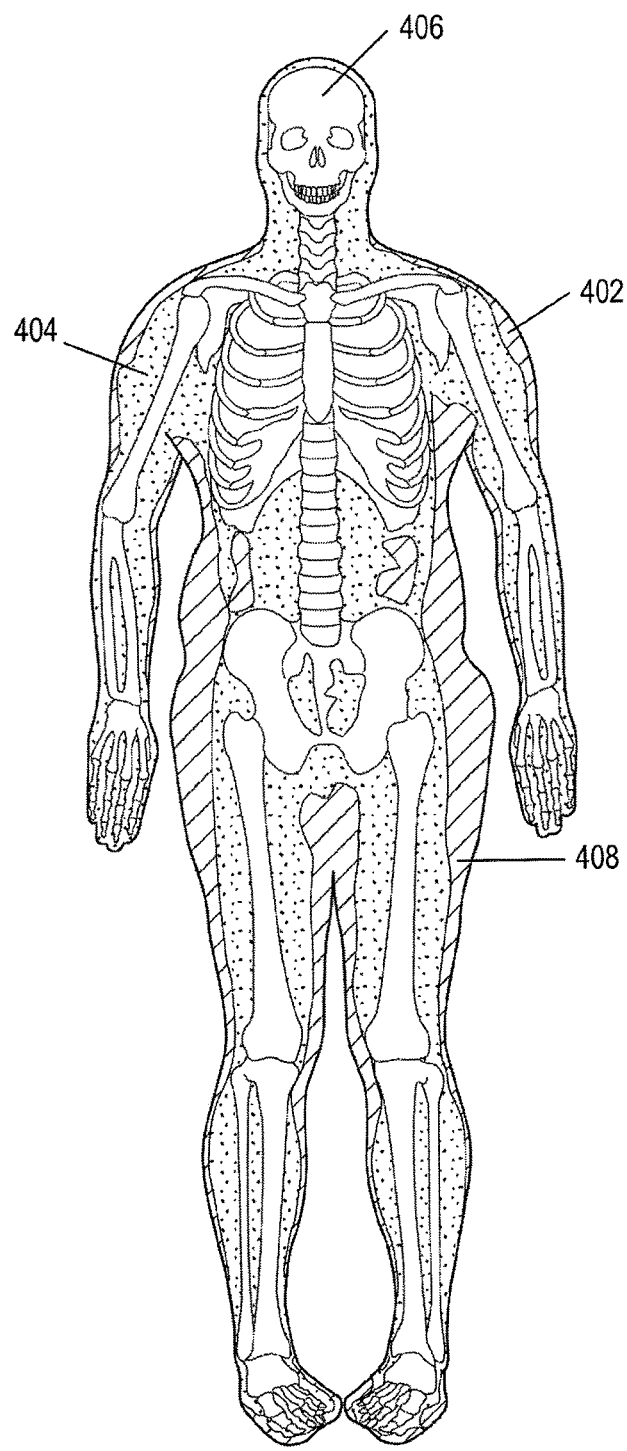
FIG. 4 depicts an image from a scan of a relatively fit, but overweight young male depicting tissue components therein.
Figure 5:
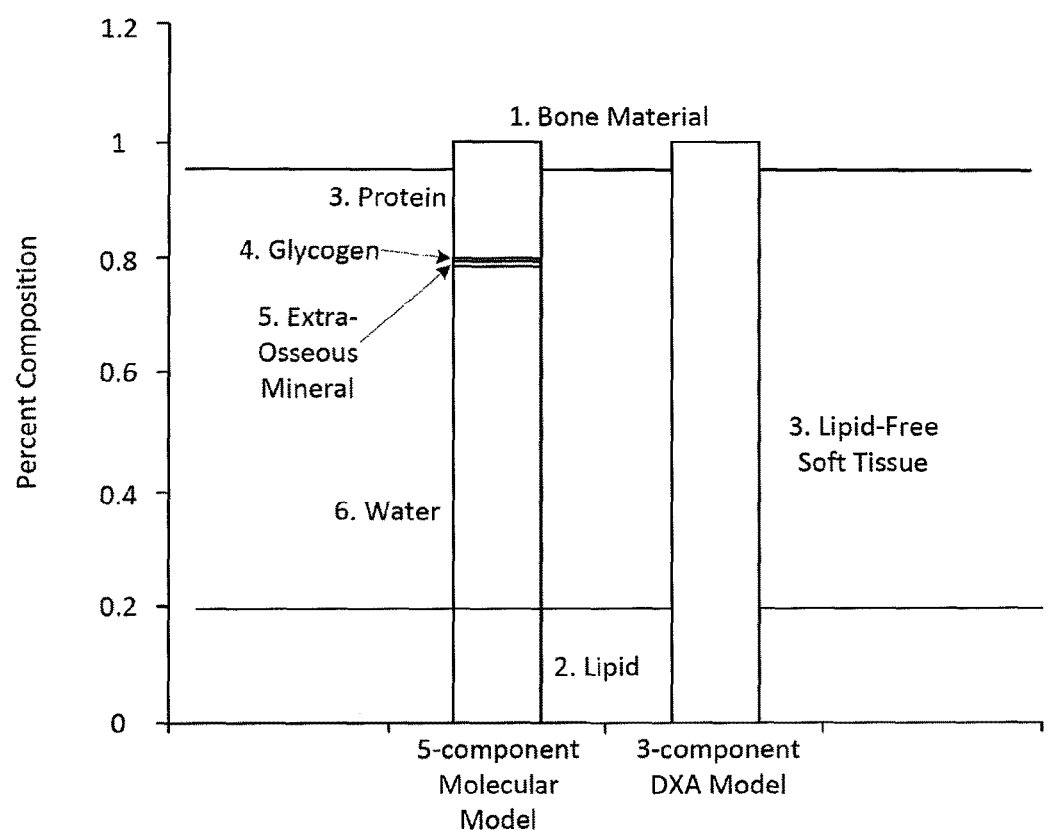
FIG. 5 depicts a five component molecular model of body composition compared to a three component molecular model.

As an example, FIG. 4 depicts a scan of a relatively fit, but overweight young male depicting such components therein. The different stippling and hashed lines identify fat tissue (hash lines, 402), lean tissue (stippling, 404), and BMC (white, 406). A sample colored version of such a similar scan can be found in Carla M. M. Prado, Steven B. Heymsfield, *Lean Tissue Imaging: A New Era for Nutritional Assessment and Intervention*, JPEN J Parenter Enteral Nutr. 2014; 38(8):940-953, the disclosure of which is incorporated by reference herein in its entirety. Simplifying a human body into three components or categories, however, is an imperfect approximation as the human body is complex. Such an approximation is helpful, however, in making some determinations, such as relative locations of lean tissue and bones, bone densities, and so on. The approximation does have limitations, however, in using the above referenced systems to identify other physiological conditions or properly determine tissue amounts in patients having those physiological conditions. For instance, FIG. 5 shows some of the complexities and potential errors in approximating tissue types into only three categories. Additional information regarding FIG. 5 can be found in IAEA Human Health Series No. 15 "Dual Energy X-ray for bone density and body composition assessment" found at www.iaea.org/Publications/index.html, the disclosure of which is hereby incorporated by reference herein in its entirety.

In approximating an amount of lean tissue, it is useful to understand that lean tissue is composed primarily of water. In a patient with a fairly stable level of hydration, the lean tissue determination discussed above works reasonably well as a surrogate for muscle mass. Various pathological conditions and situations, however, cause the lean tissue determination to no longer be a good surrogate for muscle mass. For example, edema in appendages of the patient, such as the legs and arms, may cause a significant divergence from lean tissue determinations and muscle mass locally in the appendage. When analyses or treatments of other ailments rely on the lean tissue determination, those analyses will similarly be inaccurate due to the error. For instance, the error is particularly an issue in the diagnosis of Sarcopenia, which is a degenerative loss of skeletal muscle mass, quality, and strength. Sarcopenia is a component of the frailty syndrome and is associated with aging and other pathologies. Proper diagnosis of Sarcopenia depends on an accurate measurement of appendicular muscle mass in aged persons. This same population, however, can commonly have edema, thus confounding the measurements obtained by imaging systems such as those referenced and described herein.

The technologies further described herein allow for a more accurate measurement of muscle mass, including in the legs and arms, even in the presence of edema. Within the body, areas that are primarily fat tissue without overlapping muscle tissue can be analyzed using the dual energy radiation techniques above to identify an amount of fat tissue and an amount of water, potentially representative of edema. In most individuals, the body has a layer of nearly pure fat cells just under the skin, termed "subcutaneous fat." In the projected image of FIG. 4, the subcutaneous fat portion 408 is substantially free of muscle. The subcutaneous fat is often a good primary fat target for analysis. The amount of water or degree of edema is determined based on an analysis of the primary fat target, and that determination is used to correct a lean tissue measurement for edema or water content. Of note, fat cells in fat tissue are not 100% lipid because they contain water and other non-lipid components.

In an example, a correction for the presence of edema may be obtained by determining an amount or percentage of fat in the subcutaneous fat layer in an appendage of the patient, such as an arm or a leg. The amount of fat or percentage of fat determination is compared to a predetermined or predefined standard. Such standards may be, for example, the expected fat percentage or amount of fat of the subcutaneous fat from an individual known to not have edema, or the fat percentage or fat amount measured in another part of the body of the same patient, such as the subcutaneous fat of the abdominal area. The standard amount of fat or fat percentage standard is referred to herein as the "reference amount".

Based on the comparison of the fat amount or fat percentage for the particular patient to the reference amount, a correction for edema or other physiological conditions may be made to the lean component of the measurement in the appendage from which the primary fat target was located. For example, lean mass for a particular appendage could be corrected based on the difference of the measured fat percentage of the patient's subcutaneous tissue to the reference amount percentage of fat. In some examples, the correction is a multiplicative factor times the lean mass of the limbs based on a functional relationship between the measured fat percentage and the reference amount fat percentage. For instance, the following equation provides one example for correcting a lean tissue determination:

$$L_C = f(F_p, F_S) \times L_E \qquad (1)$$

where:
$L_C$ is the corrected lean tissue amount;
$F_p$ is the fat amount or fat percentage for the primary fat target of the patient;
$F_S$ is the standard amount of fat or the standard fat percentage; and
$L_E$ is the estimated lean tissue amount prior to correction.
The corrected lean tissue amount may also be referred to herein as muscle mass. In a particular embodiment, the equation used to correct the estimated lean mass amount is as follows:

$$L_C = \frac{F_p}{F_s} \times L_E \qquad (2)$$

Other equations and relationships to correct the estimated lean tissue amount are also contemplated.

Figure 6A:
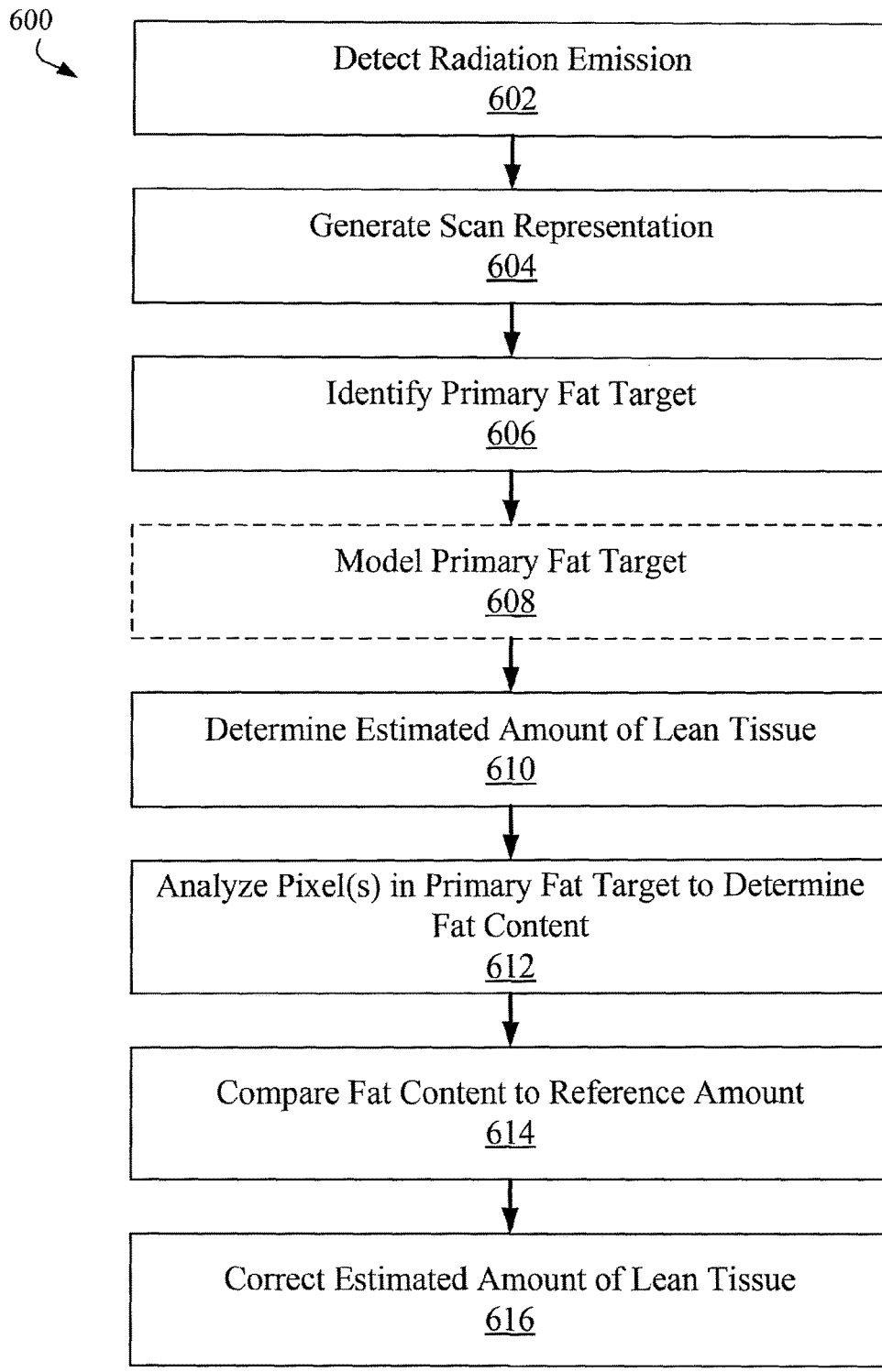
FIG. 6A depicts a method of correcting for physiological condition such as edema.

FIG. 6 depicts a method 600 for determining muscle mass of a patient by correcting an estimated lean mass. At operation 602, radiation emitted from a densitometer or dual-energy radiation device is detected. For instance, the radiation may be a beam that has passed through a patient and is detected by a detector, such as linear detector 130 as described above. Generally, imaging systems can measure fat percentage and total mass, or fat and lean mass, on a pixel-by-pixel basis, but other area measurements, such as square centimeters, may also be utilized. Based on the detected radiation emission, a scan representation is generated at operation 604. The scan representation may be for a particular region of interest of the patient, such as appendage like an arm or a leg or portions of an arm or leg. For example, because edema is normally present in the lower appendages, the area of interest may be the portion of the leg below the knee. The scan representation may also be of the whole body of the patient, similar to the scan representation in FIG. 4. In some examples, the scan representation may not be an image, but another type of representation, such as a chart, graph, or other model.

At operation 606, a primary fat target is identified in the scan representation. The primary fat target may be any portion of the body that is predominately not occupied by muscle. For example, as discussed above, a subcutaneous fat region of the patient is a suitable primary fat target. Identifying the primary fat target may also include identifying at least one pixel in the scan representation that is representative of the primary fat region. For example, in the scan representation depicted in FIG. 4, the primary fat target may be the subcutaneous fat region 408, as identified in the figure. Each pixel forming the representation of the subcutaneous fat region may be identified in operation 606, or a subset of those pixels may be determined. At operation 608, the primary fat target may be modeled to determine a mass, volume, or other characteristic of the primary fat target.

Additionally, a total water or lean tissue level of the primary fat target may be determined as part of operation 608. Of note, the lean tissue within the primary fat target is predominately water rather than muscle. The primary fat target may be modeled by determining a depth or average depth of the primary fat target from the scan representation. Alternatively or additionally, the depth of fat may be extrapolated so as to generate a substantially annular volume of the primary fat target (e.g. 360° around the appendage). Other detailed examples of modeling visceral fat are provided in U.S. Pat. No. 7,725,153 and U.S. Patent Publications 2010/0234,719 and US 2011/0235,886, the disclosures of which are hereby incorporated by reference herein in their entireties.

Figure 6B:
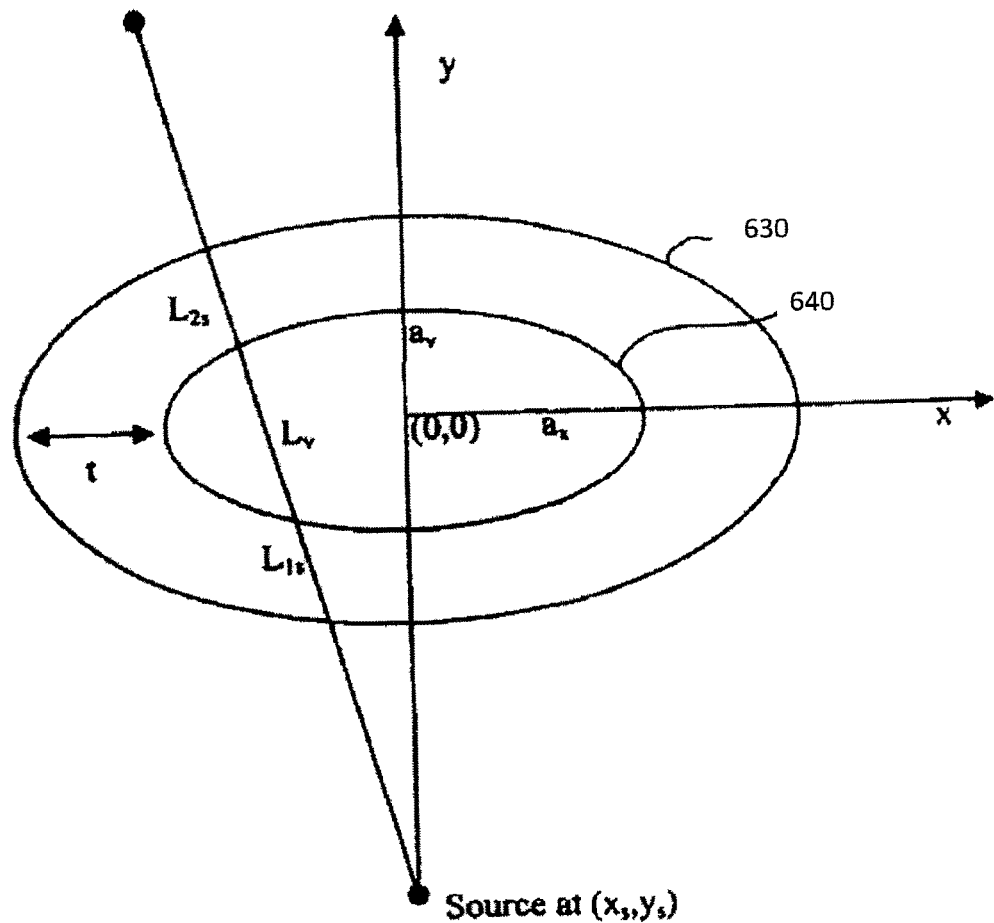
FIG. 6B depicts a geometrical model for modeling a primary fat target.

As an example, FIG. 6B illustrates geometry related to modeling a primary fat target. The outline of the region of interest is approximated by an ellipse 630 and the inner outline of the primary fat target is approximated by a concentric inner ellipse 640. The primary fat target is between the two ellipses. As discussed above, where the subcutaneous fat region is the subcutaneous fat region of an appendage, it generally wraps around the appendage, similar to an ellipse. Let ray i be the line connecting source point $(x_s, y_s)$ of a fan beam of x-rays to detector point $(x_d, y_d)$. The total length of intersection of the line with the concentric ellipses is given by $$L = L_{1s} + L_{2s} + L_v \qquad (3)$$

Where $L_{1s} + L_{2s} = L_s$, the total length of the line i through subcutaneous fat, and $L_v$ is the length of the same line i through the tissue surrounded by the subcutaneous fat. The pertinent line lengths can be calculated or estimated as discussed below, or in some other way based on known parameters such as the positions of the source and detector relative to ellipses 630 and 640.

The fat percentage (% $Fat_{vi}$) in the central region for the raypath that is along line i and is from the source focal spot to a detector position that corresponds to a dual energy x-ray measurement for a pixel in the image will be $$\% \ Fat_{vi} = (\text{total } \% \ fat)_i L_v / L \qquad (4)$$

The quantity (total % Fat), for use in Equation 4 is estimated from the dual energy x-ray measurements for the raypath using known DXA processing.

Figure 6C:
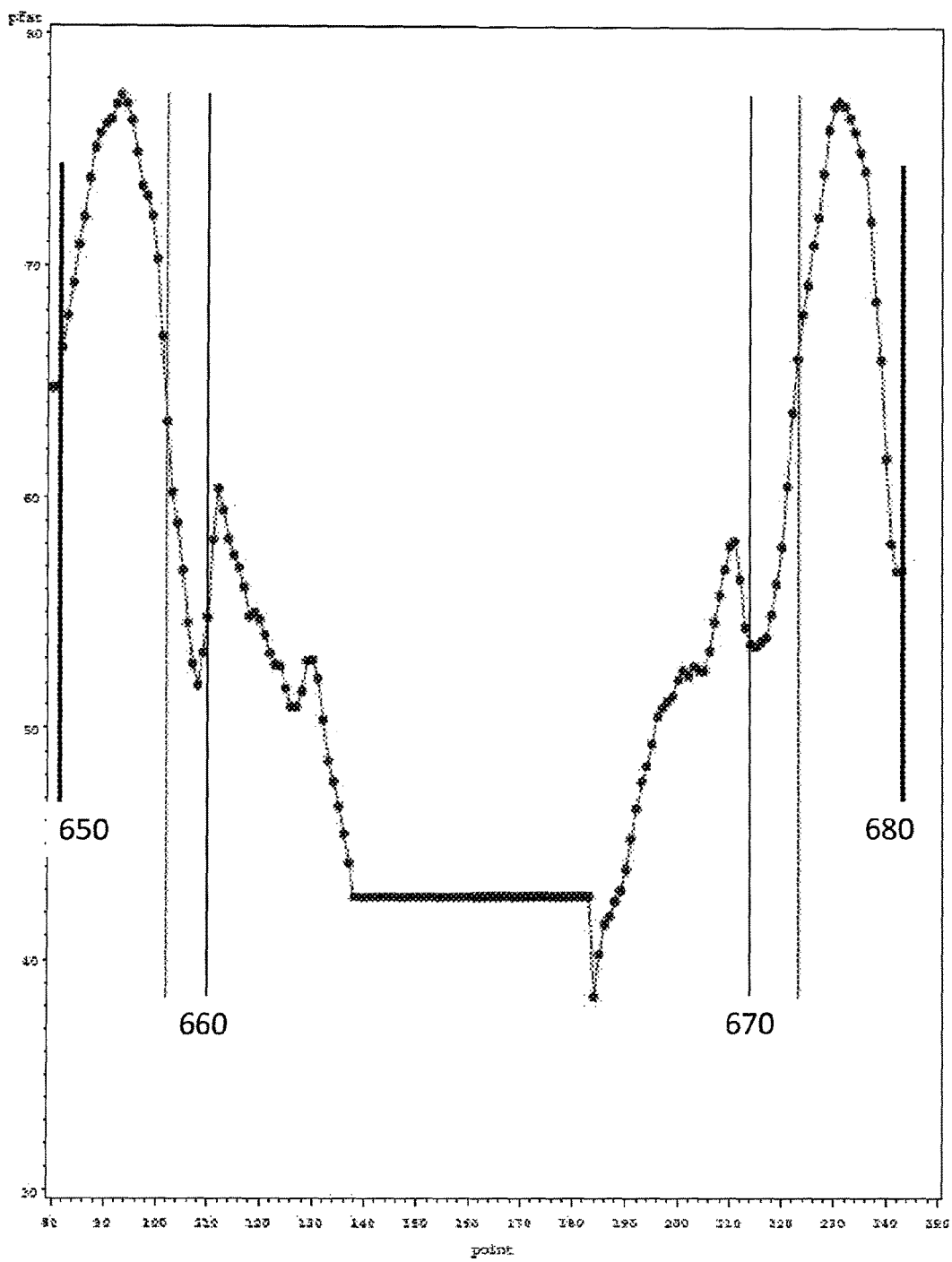
FIG. 6C depicts a plot of fat percentage by pixel.

The inner ellipse 52 may be defined by the major axes $a_x$ and $a_y$, and the outer ellipse defined by $b_x$ and $b_y$. The parameters can then be estimated from a profile plot of the fat percentage vs. pixel number as illustrated in FIG. 6C, with any needed accounting for geometric factors related to using a fan beam of x-rays. The total lengths of the subcutaneous fat regions ($L_{1s}$, $L_{2s}$) may be calculated based on:

$$L_{1s} + L_{2s} = L - \sqrt{(x_2 - x_1)^2 + (y_2 - y_1)^2} \qquad (5)$$

The equation may be solved using a number of mathematical techniques, including those discussed in U.S. Pat. No. 7,725,153. For example, the following sets of equations representing the right-hand side of the Equation 5 can be used to solve for the lengths based on data in a plot such as the one in FIG. 6C.

$$\begin{cases} x_2 = x_s + t_2 d_s \\ y_2 = y_s + t_2 d_y \\ x_1 = x_s + t_1 d_x \\ y_1 = y_s + t_1 d_y \end{cases} \qquad \text{Eq. Set. 6}$$

-continued $$\begin{cases} t_1 = \left(-R + \sqrt{P}\right)/F \\ t_2 = \left(-R - \sqrt{P}\right)/F \end{cases} \quad \text{Eq. Set. 7}$$

$$\begin{cases} P = R^2 + F - FG \\ R = d'_x x'_s + d'_y y'_s \\ F = (d'_x)^2 + (d'_y)^2 \\ G = (x'_s)^2 + (y'_s)^2 \end{cases} \quad \text{Eq. Set. 8}$$

$$\begin{cases} x'_s = \dfrac{x_s}{a_x} \\ y'_s = \dfrac{y_s}{a_y} \\ d'_x = \dfrac{d_x}{a_x} \\ d' = \dfrac{d_y}{a_y} \\ d_x = x_d - x_s \\ d_y = y_d - y_s \end{cases} \quad \text{Eq. Set. 9}$$

In addition the width of the anterior and posterior sections of a subcutaneous fat region may be determined by analyzing the representative scan, such as the one shown in FIG. 4, as discussed below. Such widths could then be used to approximate the ellipse shown in FIG. 6B through various mathematical techniques.

FIG. 6C illustrates a fat percentage estimated from DXA measurements for pixel positions in a DXA image. The horizontal axis is the pixel number in the DXA image across the width of a region of interest of the patient. The vertical axis is the fat percentage. The vertical axis represents the total fat percentage for the respective pixel positions, and thus typically includes the entire region of interest, such as an appendage. For instance, it is the percentage of fat in the tissue that is along the x-ray beam path from the source to the x-ray detector element(s) that corresponds to a pixel in the image. The shoulders of the curve between 650 and 660 and 670 and 680 represent a subcutaneous fat region for the patient. Where the pixel width is known, the width of the subcutaneous region may be determined. In addition, the percentage of lean tissue for the subcutaneous region may also be determined from the plot in FIG. 6C by subtracted from the displayed fat percentage as the subcutaneous fat region should only include fat tissue and lean tissue.

Returning to FIG. 6A, at operation 610, an estimated amount of lean tissue is determined. The estimated amount of the lean tissue may also be based in part on the primary fat target model generated in operation 608.

As an example, the width of the primary fat target, such as the subcutaneous fat region, is determined at each height (H) of the limb on the posterior (p) and anterior (a) sides of the limb from the far extremity, such as toes or fingers or a foot or a hand, to the trunk. For example, for a leg, the width of the subcutaneous fat region changes between the ankle, the hip, or the knee. As such, measurements or estimates of the width of the fat layer may be taken at different heights to more accurately predict the shape and overall size of the subcutaneous fat region. The width of the subcutaneous fat region on the posterior side for a particular level may be represented as $w_s^p(H)$, and the width of the subcutaneous fat region on the posterior side for a particular level may be represented as $w_s^a(H)$. In some embodiments, the width of the limb ($w_l(H)$) at a particular level is measured from the image. In such embodiments, the width of the skeletal muscle ($w_m(H)$) at each level may be estimated by the following equation:

$$w_m(H) = w_l(L) - [w_s^p(H) + w_s^a(H)] \quad (10)$$

The lean tissue of the skeletal muscle at level L is can be estimated with a DXA machine by analyzing the pixels representing the skeletal muscle. By including only the skeletal muscle pixels in determining the lean mass, the lean mass estimation is more likely to be representative of muscle mass.

Additionally, the fat mass of the limb at a given level may be approximated by an annulus of an ellipse, as a DXA machine is capable of measuring thickness (t) and widths with substantial accuracy. Based on the determined or measured widths or thicknesses, the subcutaneous fat can be modeled as a ring of fat encompassing the skeletal muscle.

In another example, determining an estimated amount of lean tissue may include removing the modeled primary fat target prior to analyzing the scan representation to determine an estimated amount of lean tissue. For instance, due to the subcutaneous fat wrapping around the skeletal muscle, the lean tissue (primarily water) may be included in the total lean mass estimation because the radiation passes through the whole region of interest. Accordingly, removing the modeled subcutaneous fat region from the analysis improves the estimation of muscle mass. Similarly, determining an estimated amount of lean tissue may also include removing the amount of water or lean tissue determined to be in the primary fat target, as that water or lean tissue may otherwise be inadvertently included in the lean mass determination and eventually in an estimation of muscle mass.

At operation 610, pixels of the primary fat target are analyzed to determine fat content within the primary fat target. In some embodiments, a single pixel within the primary fat target portion of scan representation may be analyzed to determine an amount of fat or a fat percentage for that pixel. In other embodiments, additional pixels representative of the primary fat target are also analyzed to determine an amount of fat or a fat percentage for those pixels. In such embodiments, the fat amount for each pixel may be summed and/or the fat percentages for the pixels may be averaged to determine an overall fat percentage for the primary fat target.

Once a fat amount or fat percentage for the primary fat target has been determined, that fat amount or fat percentage is compared to a reference amount at operation 614. As discussed above, the reference amount may be determined from a sample of patients not having edema. The reference amount may also be from another portion of the patient where edema is known to not be present. For example, in many elderly patients, subcutaneous fat may be located about the torso or midsection of the patient, while the appendages lack subcutaneous fat. Under such circumstances, the primary fat target may be proximate the torso and compared to reference amounts obtained from the appendages. Other reference amounts may be determined so as to represent a relatively healthy individual without edema. The reference amount may also be from a previous scan of the patient when it was known that the patient did not have edema.

Based on the comparison in operation 614, the estimated amount of lean tissue is corrected in operation 616. By correcting the estimated amount of lean tissue, a more accurate representation of the muscle mass for the patient is generated. The correction to the estimated amount of lean tissue may be accomplished by using equations (1) or (2)

discussed above, or variations thereof. Other suitable correction factors based on the comparison in operation 614 are also contemplated. For instance, the lean tissue estimation may be corrected based on the following equation:

$$(w_s^p((L)+w_s^a(L)) \times w_m(L) \times E \qquad (11)$$

where E is an edema correction derived by comparing a fat percentage of the primary fat target to a reference amount, such as a value derived by measuring a population of persons known not to have edema or a value obtained by measuring fat somewhere else on the person which has no edema or at least much less edema than the appendage being measured.

In some embodiments, the comparison operation 614 may not be performed, and a correction to the lean mass estimation may be made without reliance on such a comparison. For example, a correction for the hydration of the fat mass ($E_f$) and a correction of the hydration of the lean mass ($E_l$) may be utilized. The correction values $E_f$ and $E_l$ are derived from a determination of the fat percentage or fat amount of the primary fat target. The muscle mass (MM) may be determined according to the following equation:

$$MM = M_l - M_f E'_f \qquad (12)$$

where $M_l$ is the estimated lean mass, $M_f$ is the estimated fat mass as determined by the DXA machine, and $E'_f$ is a percentage of lean mass in the primary fat target. In some embodiments, a correction of the hydration of the lean mass ($E_l$) may be utilized. The following equation is representative of such an embodiment:

$$MM = E_1(M_1 - M_f E'_f) = M_l E_l - M_f E_f \qquad (13)$$

In embodiments, the correction for the hydration of the fat mass ($E_f$) and the correction of the hydration of the lean mass ($E_l$) may be proportional to one another. In embodiments where the hydration of the fat mass is similar to the hydration of the muscle mass, both $E_f$ and $E_l$ may be represented by $E'_f$. In such embodiments, the muscle mass may be determined by the following equation:

$$MM = M_l E'_f - M_f (E'_f)^2 \qquad (14)$$

Figure 7:
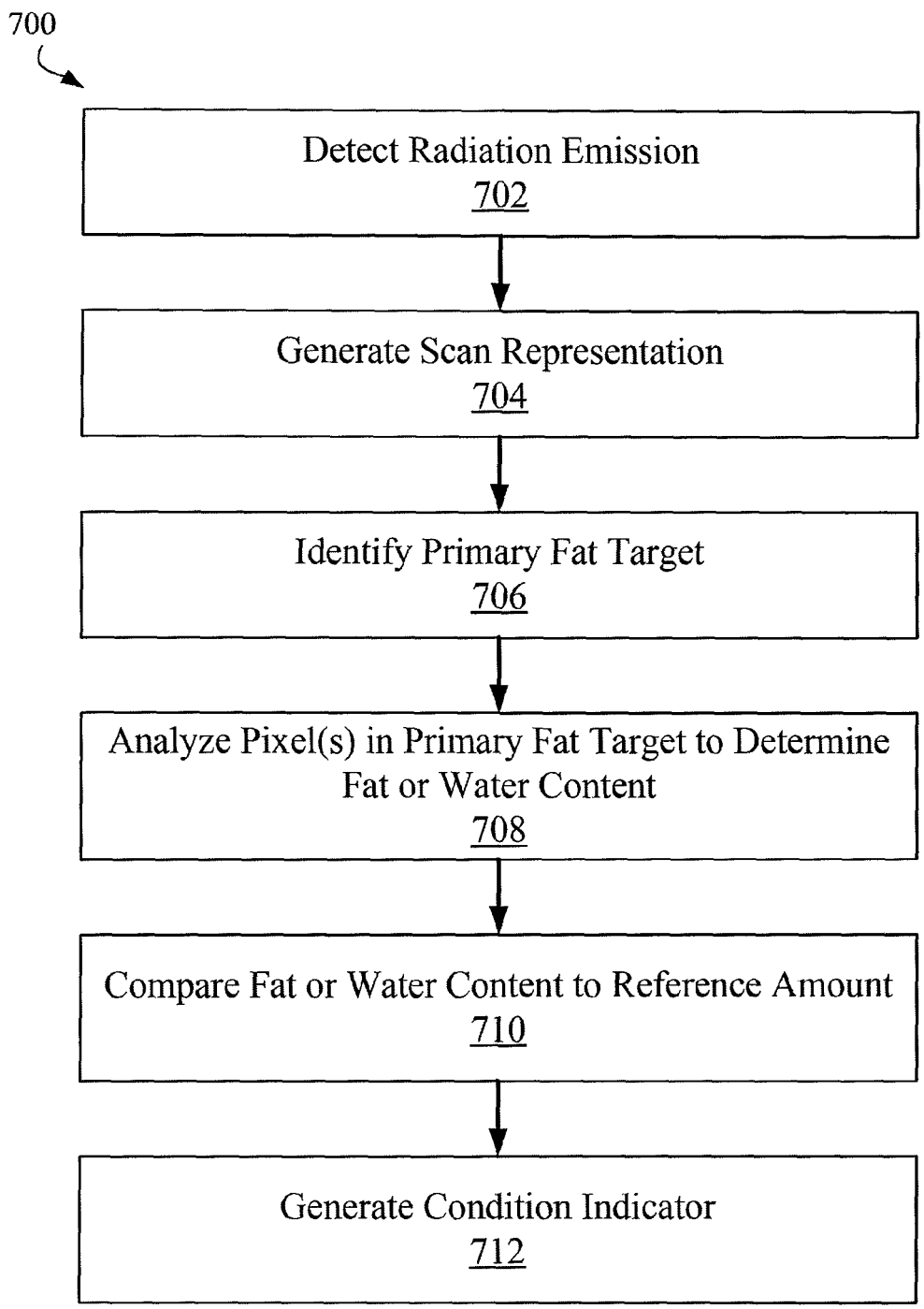
FIG. 7 depicts a method of identifying a physiological condition such as edema.

FIG. 7 depicts a method of identifying a physiological condition (e.g., edema). At operation 702, radiation emitted from a densitometer or dual-energy radiation device is detected. For instance, the radiation may be a beam that has passed through a patient a detected by a detector, such as linear detector 130 as described above. Generally, imaging systems can measure fat percentage and total mass, or fat and lean mass, on a pixel-by-pixel basis, but other area measurements, such as square centimeters, may also be utilized. Based on detected radiation emission, a scan representation is generated at operation 704. The scan representation may be for a particular region of interest of the patient, such as appendage like an arm or a leg. The scan representation may also be of the whole body of the patient, similar to the scan representation in FIG. 4. In some embodiments, the scan representation may not be an image, but another type of representation, such as a chart, graph, or other model.

At operation 706, a primary fat target is identified in the scan representation. The primary fat target may be any portion of the body that is predominately not occupied by muscle. For example, as discussed above, a subcutaneous fat region of the patient is a suitable primary fat target. Identifying the primary fat target may also include identifying at least one pixel in the scan representation that is representative of the primary fat region. For example, in the scan representation depicted in FIG. 4, the primary fat target may be the subcutaneous fat region as identified in the figure. Each pixel forming the representation of the subcutaneous fat region may be identified in operation 706, or a subset of those pixels may be identified.

At operation 708, pixels of the primary fat target are analyzed to determine fat content or water content within the primary fat target. The fat content may be a fat amount or a fat percentage. The water content may be a water amount or a water percentage. In some embodiments, a single pixel within the primary fat target portion of scan representation may be analyzed to determine a fat content or a water content for that pixel. In other embodiments, additional pixels representative of the primary fat target are also analyzed to determine a fat content or water content for those pixels. In such embodiments, the fat content or water content for each pixel may be summed and/or the fat percentages for the pixels may be averaged to determine an overall fat percentage for the primary fat target.

The fat content or water content determined in operation 708 is then compared to a reference amount at operation 710. As discussed above, the reference amount may be determined from a sample of patients not having the physiological condition. The reference amount may also be from another portion of the patient known not to display the condition (e.g., as described above in regard to subcutaneous fat in the torso area, but not appendages). Other reference amounts may be determined so as to represent a relatively healthy individual without the physiological condition. The reference amount may also be from a previous scan of the patient when it was known that the patient did not have the physiological condition.

Based on the results of the comparison, a condition indicator is generated at operation 712. The condition indicator indicates whether the patient has the physiological condition being tested. For example, if the results of the comparison at operation 710 reveal that the fat content in the primary fat target is below the reference fat amount, a condition indicator may be generated indicating that the patient has edema. In some embodiments, the fat content must be a certain amount below the reference fat amount before a condition indicator indicating edema will be generated. For instance, the edema condition indicator may only be generated if the fat content is a standard deviation below the reference fat amount. Where the primary fat target is being tested for only a region of interest, the condition indicator indicates that the patient has localized edema in the region of interest. Similarly, if the water content is above the reference water amount, a condition indicator may be generated indicating that the patient has edema. In some embodiments, the water content must be a certain amount above the reference water amount before a condition indicator indicating edema will be generated. For instance, the edema condition indicator may only be generated if the fat content is a standard deviation above the reference water amount. The condition indicator may be a screen item in a user interface or other indicator suitable to convey the physiological condition of the patient.

As discussed above, the method 600 and the method 700 may be performed for a region of interest or for the whole body of the patient. In embodiments where the methods are performed for the region of interest, the primary fat target and the pertinent lean tissue are located within the same region of interest, such as an arm of the patient. In embodiments where the methods are performed for the whole body, the primary fat target and the pertinent lean tissue may be located in any portion of the body. In some patients, however, the patient may not have a suitable primary fat target in the region of interest. For example, elderly patients may have minimal to no subcutaneous fat in their legs. For such patients, the primary fat target may be the subcutaneous fat of the abdomen, and the results obtained from analysis of the abdominal fat may be used to correct an estimated lean tissue amount in a separate region of interest, such as the leg, as described above.

Other techniques to correct lean mass estimations for edema may be based on the shape of the soft tissue versus, for example, the expected shape of the same tissue. That is, a limb where edema is present will look swollen, as compared to a limb where edema is not present. Bone landmarks may also be used as a basis for correction. For example, the position of knee relative to the outer contours of the leg may indicate the presence of edema as well.

Other techniques for correcting for the presence of edema include measuring the soft tissue area around the ankles, outside of the bone. This measurement may then be compared to the shape of the thigh, to detect and correct for swelling due to edema. In other techniques, multi-frequency bioelectric impedance may be used to measure the water content of the legs and/or arms, and use that to make an edema correction. Still another technique utilizes "water dilution," which can very accurately measure total body water, so as to perform an overall hydration correction to the lean mass. In water dilution, a patient drinks a known quantity of deuterated water, and after a suitable time for this to disperse through the body, a saliva sample is taken and the percentage of deuterated water of the saliva sample, along with the patient's mass, can be used to measure total water hydration.

Figure 8:
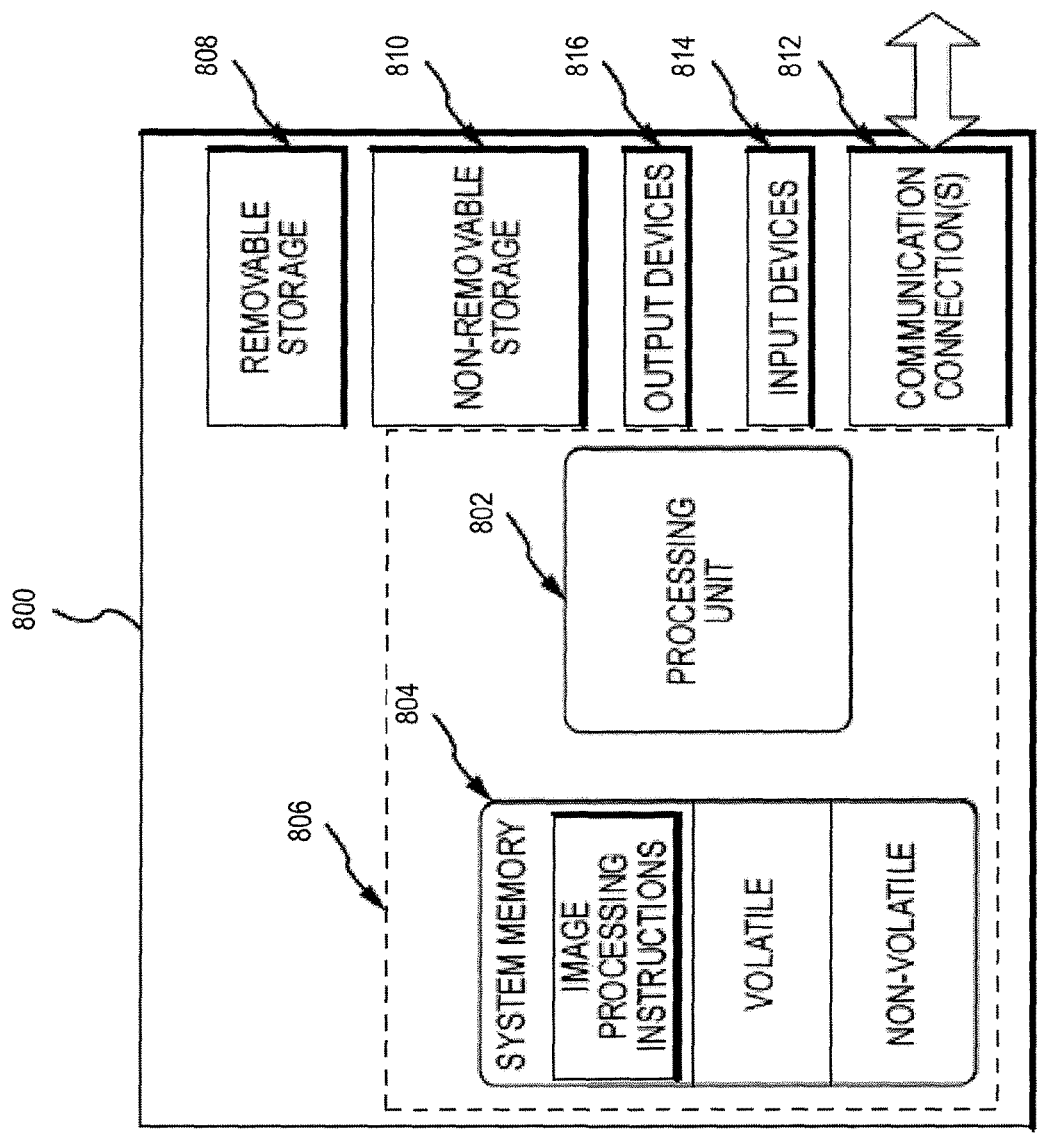
FIG. 8 illustrates one example of a suitable operating environment in which one or more of the present examples can be implemented.

FIG. 8 illustrates one example of a suitable operating environment 500 in which one or more of the present embodiments can be implemented. This operating environment may be incorporated directly into a scanning system, or may be incorporated into a computer system discrete from, but used to control, a scanning system such as described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 800 typically includes at least one processing unit 802 and memory 804. Depending on the exact configuration and type of computing device, memory 804 (storing, among other things, instructions to perform the image acquisition and processing methods disclosed herein) can be volatile (such as RAM), non-volatile (such as ROM, flash memory, etc.), or some combination of the two. This most basic configuration is illustrated in FIG. 8 by dashed line 806. Further, environment 800 can also include storage devices (removable, 808, and/or non-removable, 810) including, but not limited to, magnetic or optical disks or tape. Similarly, environment 800 can also have input device(s) 814 such as touch screens, keyboard, mouse, pen, voice input, etc., and/or output device(s) 816 such as a display, speakers, printer, etc. Also included in the environment can be one or more communication connections 812, such as LAN, WAN, point to point, Bluetooth, RF, etc.

Operating environment 800 typically includes at least some form of computer readable media. Computer readable media can be any available media that can be accessed by processing unit 802 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 800 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by computer system 800 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 800 is part of a network that stores data in remote storage media for use by the computer system 800.

Figure 9:
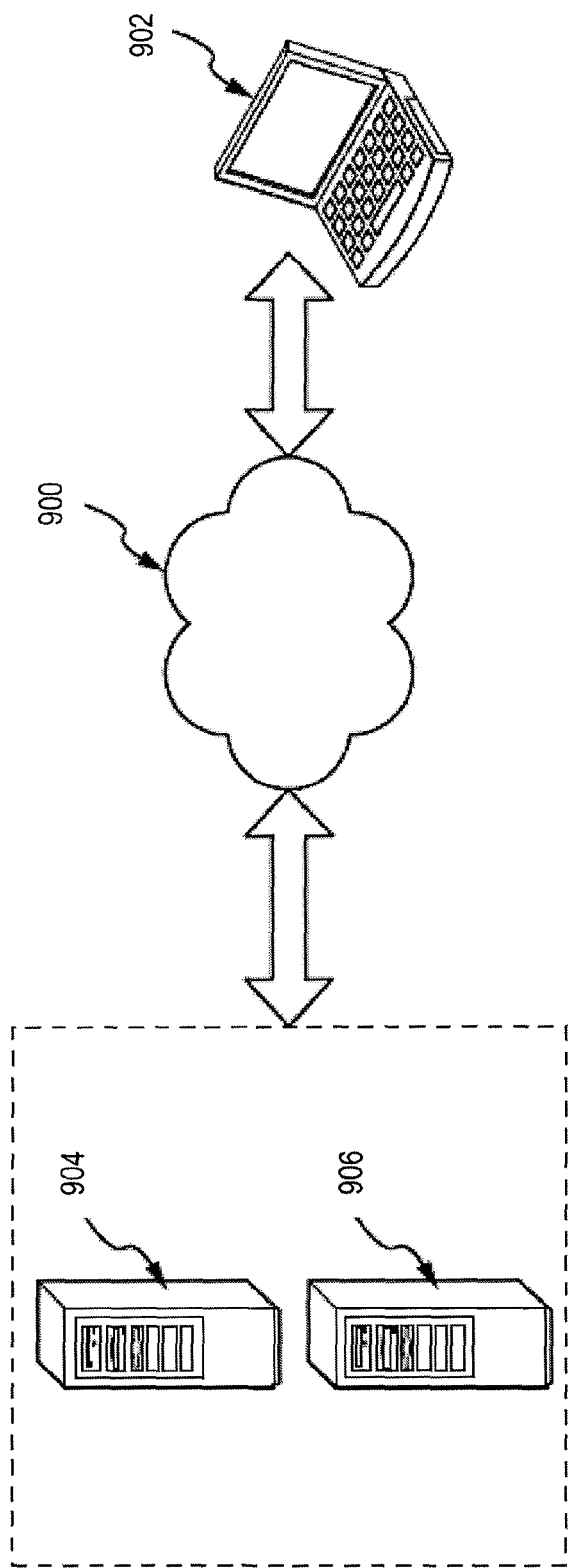
FIG. 9 is an embodiment of a network in which the various systems and methods disclosed herein may operate.

FIG. 9 is an embodiment of a network 900 in which the various systems and methods disclosed herein may operate. In embodiments, a client device, such as client device 902, may communicate with one or more servers, such as servers 904 and 906, via a network 908. In embodiments, a client device may be a laptop, a personal computer, a smart phone, a PDA, a netbook, or any other type of computing device, such as the computing device in FIG. 8. In embodiments, servers 904 and 906 may be any type of computing device, such as the computing device illustrated in FIG. 8. Network 908 may be any type of network capable of facilitating communications between the client device and one or more servers 904 and 906. Examples of such networks include, but are not limited to, LANs, WANs, cellular networks, and/or the Internet.

In embodiments, the various systems and methods disclosed herein may be performed by one or more server devices. For example, in one embodiment, a single server, such as server 904 may be employed to perform the systems and methods disclosed herein, such as the method for scanning and image processing. Client device 902 may interact with server 904 via network 908. In further embodiments, the client device 902 may also perform functionality disclosed herein, such as scanning and image processing, which can then be provided to servers 904 and/or 906.

In alternate embodiments, the methods and systems disclosed herein may be performed using a distributed computing network, or a cloud network. In such embodiments, the methods and systems disclosed herein may be performed by two or more servers, such as servers 904 and 906. Although a particular network embodiment is disclosed herein, one of skill in the art will appreciate that the systems and methods disclosed herein may be performed using other types of networks and/or network configurations.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. Embodiments according to the invention may also combine elements or components of those that are disclosed in general but not expressly exemplified in combination, unless otherwise stated herein. The scope of the technology is defined by the following claims and any equivalents therein.

The invention claimed is:

1. A method for determining muscle mass of a patient, the method comprising:
    detecting, by a radiation detector, a radiation emission from a densitometer passed through the patient;
    based on the detected radiation emission, generating a scan representation of a region of interest of the patient, the scan representation including one or more pixels;
    determining, by a processor, an estimated amount of lean tissue in the region of interest;
    identifying, by the processor, a primary fat target within the region of interest, wherein the primary fat target is a subcutaneous fat region;
    identifying, by the processor, a pixel in the scan representation representative of the primary fat target;
    analyzing, by the processor, the pixel representative of the primary fat target to determine an amount of fat in the primary fat target;
    comparing, by the processor, the determined amount of fat to a reference amount;
    correcting, by the processor, the estimated amount of lean tissue based at least in part on the comparison to generate a corrected muscle mass value for the region of interest of the patient; and
    displaying the corrected muscle mass value for the region of interest.

2. The method of claim 1, further comprising analyzing the pixel representative of the primary fat target to determine an amount of water present in the primary fat target.

3. The method of claim 1, further comprising:
    determining a model of the primary fat target based on at least a depth of the primary fat target; and
    subtracting the modeled primary fat target from the estimated amount of lean tissue.

4. The method of claim 1, wherein the correcting the estimated amount of lean tissue is based on the following equation, $L_c = f(F_p, F_s) \times L_E$, where $L_c$ is the corrected muscle mass value, $F_p$ is the amount of fat in the primary fat target, $F_s$ is the reference amount, and $L_g$ is the estimated amount of lean tissue.

5. The method of claim 1, wherein the region of interest is a torso region of the patient.

6. The method of claim 1, wherein the region of interest is an appendage of the patient.

7. The method of claim 1, wherein the reference amount is determined from a set of sample persons.

8. A system for determining muscle mass of a patient, the system, comprising:
    a densitometer;
    a radiation detector;
    at least one processor;
    memory, operatively connected to the at least one processor, storing instructions that when executed by the at least one processor cause the system to perform a set of operations comprising:
        detecting, by the radiation detector, a radiation emission from the densitometer passed through the patient;
        based on the detected radiation emission, generating a scan representation of a region of interest of the patient, the scan representation including one or more pixels;
        determining an estimated amount of lean tissue in the region of interest;
        identifying a primary fat target within the region of interest, wherein the primary fat target is a subcutaneous fat region;
        identifying a pixel in the scan representation representative of the primary fat target;
        analyzing the pixel representative of the primary fat target to determine an amount of fat in the primary fat target;
        comparing the determined amount of fat to a reference amount;
        correcting the estimated amount of lean tissue based at least in part on the comparison to generate a corrected muscle mass value for the region of interest of the patient; and
        displaying the corrected muscle mass value for the region of interest.

9. The system of claim 8, wherein the set of operations further comprises analyzing the pixel representative of the primary fat target to determine an amount of water present in the primary fat target.

10. The system of claim 8, wherein the set of operations further comprise:
   determining a model of the primary fat target based on at least a depth of the primary fat target; and
   subtracting the modeled primary fat target from the estimated amount of lean tissue.

11. The system of claim 8, wherein the region of interest is a torso region of the patient.

12. The system of claim 8, wherein the correcting the estimated amount of lean tissue is based on the following equation, $L_c=f(F_p,F_s) \times L_E$, where $L_c$ is the corrected muscle mass value, $F_p$ is the amount of fat in the primary fat target, $F_s$ is the reference amount, and $L_E$ is the estimated amount of lean tissue.

13. The system of claim 8, wherein the first region is a torso region of the patient and the second region is an appendage of the patient.

14. The system of claim 8, wherein the region of interest is an appendage of the patient.

15. The system of claim 8, wherein the reference amount is determined from a set of sample persons.

16. A system for determining muscle mass of a patient, the system, comprising:
   at least one processor;
   memory, operatively connected to the at least one processor, storing instructions that when executed by the at least one processor cause the system to perform a set of operations comprising:
      based on a detected radiation emission, generating a scan representation of a region of interest of the patient, the scan representation including one or more pixels;
      determining an estimated amount of lean tissue in the region of interest;
      analyzing a pixel representative of a primary fat target to determine an amount of fat in the primary fat target, wherein the primary fat target is a subcutaneous fat region in the region of interest;
      comparing the determined amount of fat to a reference amount;
      correcting the estimated amount of lean tissue based at least in part on the comparison to generate a corrected muscle mass value for the region of interest of the patient; and
      displaying the corrected muscle mass value for the region of interest.

17. The system of claim 16, further comprising:
   a densitometer;
   a radiation detector; and
   wherein the set of operations further comprises:
      emitting, by the densitometer, the radiation emission; and
      detecting, by the radiation detector, the radiation emission from the densitometer.

18. The system of claim 16, wherein the set of operations further comprises analyzing the pixel representative of the primary fat target to determine an amount of water present in the primary fat target.

19. The system of claim 16, wherein the set of operations further comprises:
   determining a model of the primary fat target based on at least a depth of the primary fat target; and
   subtracting the modeled primary fat target from the estimated amount of lean tissue.

20. The system of claim 16, wherein the reference amount is determined from a set of sample persons.

* * * * *

UNITED STATES PATENT AND TRADEMARK OFFICE
CERTIFICATE OF CORRECTION

PATENT NO. : 10,499,865 B2  
APPLICATION NO. : 15/553748  
DATED : December 10, 2019  
INVENTOR(S) : Kevin Wilson et al.

It is certified that error appears in the above-identified patent and that said Letters Patent is hereby corrected as shown below:

On the Title Page

Item (60), Delete:  
"Related U.S. Application Data  
(60) Provisional application No. 61/121,197, filed on Feb. 26, 2015."

And insert therefor:  
--Related U.S. Application Data  
(60) Provisional application No. 62/121,197, filed on Feb. 26, 2015.--

Signed and Sealed this  
Sixteenth Day of November, 2021

Drew Hirshfeld  
*Performing the Functions and Duties of the*  
*Under Secretary of Commerce for Intellectual Property and*  
*Director of the United States Patent and Trademark Office*